United States Patent
Kang et al.

(10) Patent No.: US 11,780,796 B2
(45) Date of Patent: Oct. 10, 2023

(54) METHOD OF DECOMPOSING PHENOLIC BY-PRODUCT

(71) Applicant: LG CHEM, LTD., Seoul (KR)

(72) Inventors: Min Suk Kang, Daejeon (KR); Sang Beom Lee, Daejeon (KR); Chi Hyun Jang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/606,369

(22) PCT Filed: Nov. 23, 2020

(86) PCT No.: PCT/KR2020/016593
§ 371 (c)(1),
(2) Date: Oct. 25, 2021

(87) PCT Pub. No.: WO2021/261681
PCT Pub. Date: Dec. 30, 2021

(65) Prior Publication Data
US 2022/0251012 A1    Aug. 11, 2022

(30) Foreign Application Priority Data

Jun. 23, 2020 (KR) .......................... 10-2020-0076528

(51) Int. Cl.
| | | |
|---|---|---|
| *C07C 1/20* | (2006.01) | |
| *C07C 37/00* | (2006.01) | |
| *C07C 37/52* | (2006.01) | |
| *C07C 4/22* | (2006.01) | |
| *C07C 37/72* | (2006.01) | |

(52) U.S. Cl.
CPC ................ *C07C 37/72* (2013.01); *C07C 1/20* (2013.01); *C07C 4/22* (2013.01); *C07C 37/005* (2013.01); *C07C 37/52* (2013.01)

(58) Field of Classification Search
CPC .. C07C 37/72; C07C 1/20; C07C 4/22; C07C 37/005; C07C 37/52
See application file for complete search history.

(56) References Cited

U.S. PATENT DOCUMENTS

| | | | |
|---|---|---|---|
| 4,158,611 A | | 6/1979 | Cooke |
| 4,339,605 A | * | 7/1982 | Ligorati .................. C07C 45/83 |
| | | | 203/91 |
| 5,064,507 A | | 11/1991 | O'Donnell et al. |

FOREIGN PATENT DOCUMENTS

| | | |
|---|---|---|
| CN | 102171172 A | 8/2011 |
| CN | 102992961 A | 3/2013 |
| CN | 110461806 A | 11/2019 |
| EP | 2 342 171 B1 | 7/2011 |
| EP | 3 680 226 A1 | 7/2020 |
| JP | 2011-500831 A | 1/2011 |
| KR | 10-0396718 B1 | 12/2003 |
| KR | 10-2006-0026476 A | 3/2006 |
| KR | 10-2017-0047030 A | 5/2017 |
| KR | 10-2018-0088700 A | 8/2018 |
| KR | 10-2019-0058273 A | 5/2019 |
| TW | 583167 B | 4/2004 |
| WO | 2010/062482 A2 | 6/2010 |

* cited by examiner

*Primary Examiner* — Rosalynd A Keys
(74) *Attorney, Agent, or Firm* — Bryan Cave Leighton Paisner LLP (57) ABSTRACT

The present disclosure relates to a method of decomposing a phenolic by-product, including: a step of feeding and thermally cracking a phenolic by-product stream to and in a decomposition apparatus, recovering an active ingredient from a top discharge stream, and discharging a high-boiling substance through a bottom discharge stream; a step of pressurizing each of a side discharge stream of the decomposition apparatus and a bottom discharge stream of the decomposition apparatus; a step of mixing the pressurized side discharge stream of the decomposition apparatus and the pressurized bottom discharge stream of the decomposition apparatus with each other to form a mixed stream; and a step of passing a part of the mixed stream through a reboiler, circulating the part of the mixed stream to the decomposition apparatus, and discharging a residual mixed stream.

12 Claims, 3 Drawing Sheets

-RELATED ART-

FIG. 3

−RELATED ART−

METHOD OF DECOMPOSING PHENOLIC BY-PRODUCT

CROSS-REFERENCE TO RELATED APPLICATIONS

The present application is a National Phase entry pursuant to 35 U.S.C. § 371 of International Application No. PCT/KR2020/016593, filed on Nov. 23, 2020, and claims the benefit of and priority to Korean Patent Application No. 10-2020-0076528, filed on Jun. 23, 2020, the entire contents of which are incorporated by reference in their entirety for all purposes as if fully set forth herein.

TECHNICAL FIELD

The present invention relates to a method of decomposing a phenolic by-product, and more particularly, to a method of reducing fouling in a reboiler of a decomposition apparatus due to a high-boiling substance and separating an active ingredient from a phenolic by-product.

BACKGROUND ART

In general, about 95% of phenol used in the world is produced by a Hock process. The Hock process is performed in three steps including: a step (1) of forming cumene by alkylation of benzene with propylene, a step (2) of oxidizing the cumene to cumene hydroperoxide (CHP) by combining the cumene and oxygen, and a step (3) of decomposing the cumene hydroperoxide into phenol and acetone by an acid decomposition reaction in the presence of an acid catalyst.

Here, in the cumene oxidation step which is the step (2), by-products such as acetophenone (AP), dimethyl benzyl alcohol (DMBA), dicumylperoxide (DCP), and dicumene (DC) are produced in addition to cumene hydroperoxide.

In addition, in the acid decomposition reaction of the cumene hydroperoxide in the step (3), by-products such as hydroxy acetone (HA), 2-methylbenzofuran (2-MBF), alpha-methyl styrene (AMS), mesityl oxide (MO), alpha-methyl styrene (AMS) dimer, and cumyl phenol (CP) are produced in addition to phenol and acetone.

Accordingly, since a product stream produced in such a reaction process is present in a state in which phenol, acetone, and various by-products are mixed with each other, a separation process for separating the phenol from the product stream is required.

The product stream is injected into a separate separation apparatus, an acetone-based mixture including unreacted cumene, acetone, alpha-methyl styrene, hydroxy acetone, and the like is separated through a top of the separation apparatus, and a phenolic mixture including phenol, a part of alpha-methyl styrene, 2-methylbenzofuran, and other by-products is separated through a bottom of the separation apparatus.

The phenolic mixture separated through the bottom of the separation apparatus is injected into a phenol column, phenol is separated through a top of the phenol column, and phenolic by-products such as dicumylperoxide, cumyl phenol, alpha-methyl styrene dimer, and tar are separated through a bottom of the phenol column.

In addition, in general, a process of producing bisphenol A (BPA) is a process of producing bisphenol A by a condensation reaction between the phenol and the acetone produced in the Hock process in the presence of an acid catalyst or a cation exchange resin.

As a result, by-products such as unreacted phenol, unreacted acetone, trisphenol (BPX), and tar are produced in the product stream produced by the bisphenol A reaction in addition to bisphenol A.

Active ingredients such as phenol, cumene, and alpha-methyl styrene may be recovered from the by-products produced in the phenol production process and the bisphenol A production process by a separate separation apparatus. Studies on a decomposition process and a decomposition apparatus that are capable of effectively recovering active ingredients have been conducted.

DISCLOSURE

Technical Problem

In order to solve the problems mentioned in the background art, an object of the present invention is to provide a method capable of obtaining a high-value active ingredient while reducing fouling in a reboiler of a decomposition apparatus due to a high-boiling substance.

Technical Solution

In one general aspect, a method of decomposing a phenolic by-product includes: a step of feeding and thermally cracking a phenolic by-product stream to and in a decomposition apparatus, recovering an active ingredient from a top discharge stream, and discharging a high-boiling substance through a bottom discharge stream; a step of pressurizing each of a side discharge stream of the decomposition apparatus and a bottom discharge stream of the decomposition apparatus; a step of mixing the pressurized side discharge stream of the decomposition apparatus and the pressurized bottom discharge stream of the decomposition apparatus with each other to form a mixed stream; and a step of passing a part of the mixed stream through a reboiler, circulating the part of the mixed stream to the decomposition apparatus, and discharging a residual mixed stream.

Advantageous Effects

According to the method of decomposing a phenolic by-product according to the present invention, when the active ingredient is obtained by decomposing the phenolic by-product, a high-value active ingredient can be obtained and a fouling cycle of the reboiler can also be extended.

DETAILED DESCRIPTION

The terms and words used in the description and claims of the present invention are not to be construed as general or dictionary meanings but are to be construed as meanings and concepts meeting the technical ideas of the present invention based on a principle that the inventors can appropriately define the concepts of terms in order to describe their own inventions in best mode.

The term "stream" in the present invention may refer to a flow of a fluid in a process, and may also refer to a fluid flowing through a pipe itself. Specifically, the "stream" may refer to both the fluid flowing through the pipe connecting respective apparatuses to each other itself and the flow of the fluid at the same time. In addition, the fluid may refer to gas or liquid.

Hereinafter, the present invention will be described in more detail with reference to FIG. 1 in order to assist in the understanding of the present invention.

According to the present invention, a method of decomposing a phenolic by-product is provided. The method of decomposing a phenolic by-product can include: a step of feeding and thermally cracking a phenolic by-product stream to and in a decomposition apparatus 100, recovering an active ingredient from a top discharge stream, and discharging a high-boiling substance through a bottom discharge stream; a step of pressurizing each of a side discharge stream of the decomposition apparatus 100 and a bottom discharge stream of the decomposition apparatus 100; a step of mixing the pressurized side discharge stream of the decomposition apparatus 100 and the pressurized bottom discharge stream of the decomposition apparatus 100 with each other to form a mixed stream; and a step of passing a part of the mixed stream through a reboiler 200, circulating the part of the mixed stream to the decomposition apparatus 100, and discharging a residual mixed stream.

According to an exemplary embodiment of the present invention, the phenolic by-product can include any one or more of a phenolic by-product produced in a phenol production process and a phenolic by-product produced in a bisphenol A production process. For example, the phenolic by-product can be a phenolic by-product, a phenolic by-product produced in a bisphenol A production process, or a mixture of a phenolic by-product and a phenolic by-product produced in a bisphenol A production process.

The phenol production process can be performed through the Hock process described above. Specifically, the phenol production process can be performed through a step of decomposing and purifying cumene hydroperoxide produced by an oxidation reaction of cumene to separate the cumene hydroperoxide into phenol and acetone. The step of decomposing and purifying the cumene hydroperoxide produced by the oxidation reaction of the cumene to separate the cumene hydroperoxide into the phenol and the acetone is a step using a cumene purification process and a phenol/acetone purification process. In this step, first, cumene is produced by an alkylation reaction between propylene and benzene, heavy/light by-products are discharged through a purification process, and the cumene is purified and separated. Subsequently, cumene hydroperoxide (CHP) is produced by an oxidation reaction of the purified cumene, phenol, acetone, α-methyl styrene (AMS), and heavy by-products are produced by a decomposition reaction of the cumene hydroperoxide (CHP) in the presence of a general acid catalyst such as sulfuric acid ($H_2SO_4$), and the α-methyl styrene (AMS) and the heavy by-products are discharged and the phenol and the acetone are purified and separated through a purification process.

Since a product stream produced in such a reaction process is present in a state in which phenol, acetone, and various by-products are mixed with each other, a separation process for separating the phenol from the product stream is required.

The product stream is injected into a separate separation apparatus, an acetone-based mixture including unreacted cumene, acetone, alpha-methyl styrene, hydroxy acetone, and the like is separated through a top of the separation apparatus, and a phenolic mixture including phenol, a part of alpha-methyl styrene, 2-methylbenzofuran, and other by-products is separated through a bottom of the separation apparatus.

The phenolic mixture separated through the bottom of the separation apparatus is injected into a phenol column, phenol is separated through a top of the phenol column, and phenolic by-products such as dicumylperoxide, cumyl phenol, alpha-methyl styrene dimer, and tar are separated through a bottom of the phenol column. As a result, the phenolic by-product produced in the phenol production process may include some active ingredients such as phenol, cumene, and alpha-methyl styrene, and tar.

In addition, the bisphenol A production process can be performed by a method of producing bisphenol A by a reaction between the phenol and the acetone produced in the Hock process described above and recovering the bisphenol A from the reaction product. Specifically, the bisphenol A production process can be performed through a step of decomposing and purifying cumene hydroperoxide produced by an oxidation reaction of cumene to separate the cumene hydroperoxide into phenol and acetone; a step of separating bisphenol A produced by a reaction between the separated phenol and acetone and decomposing a stream including unseparated bisphenol A in an aqueous alkaline solution; and a step of separating a reaction product, a phenolic by-product, and an acetone-based by-product obtained by the decomposition reaction.

The step of decomposing and purifying the cumene hydroperoxide produced by the oxidation reaction of the cumene to separate the cumene hydroperoxide into the phenol and the acetone is a step using a cumene purification process and a phenol/acetone purification process. In this step, first, cumene is produced by an alkylation reaction between propylene and benzene, heavy/light by-products are discharged through a purification process, and the cumene is purified and separated. Subsequently, cumene hydroperoxide (CHP) is produced by an oxidation reaction of the purified cumene, phenol, acetone, α-methyl styrene (AMS), and heavy by-products are produced by a decomposition reaction of the cumene hydroperoxide (CHP) in the presence of a general acid catalyst such as sulfuric acid ($H_2SO_4$), and the α-methyl styrene (AMS) and the heavy by-products are discharged and the phenol and the acetone are purified and separated through a purification process.

The step of separating the bisphenol A produced by the reaction between the separated phenol and acetone and decomposing the stream including the unseparated bisphenol A in the aqueous alkaline solution is a step using a bisphenol A (BPA) purification process. In this step, first, bisphenol A, more specifically, crude bisphenol A is produced by a reaction between the purified and separated phenol and acetone, and then bisphenol A with improved purity is produced via a crystallization process. The produced bisphenol A is separated via the BPA purification process, and a by-product including the unseparated bisphenol A is decomposed in an excessive amount of an aqueous alkaline solution having basic properties such as NaOH, KOH, or LiOH.

In the step of separating the reaction product, the phenolic by-product, and the acetone-based by-product obtained by the decomposition reaction, a stream in which the decomposition reaction is completed can be fed to the separation apparatus, the acetone-based mixture can be separated through the top of the separation apparatus, and the reaction product can be separated through the bottom of the separation apparatus. The reaction product is injected into a bisphenol A column, bisphenol A is separated through a top of the bisphenol A column, and phenolic by-products such as bisphenol A, phenol, dicumylperoxide, cumyl phenol, alpha-methyl styrene dimer, and tar are separated through a bottom of the bisphenol A column. In this case, the phenolic by-product includes active ingredients such as bisphenol A, cumene, and alpha-methyl styrene which are products in addition to tar which is an impurity.

As a result, the phenolic by-product produced in the bisphenol A production process can include some active ingredients such as phenol, cumene, and alpha-methyl styrene, and tar.

Therefore, a mixture of the phenolic by-product produced in the bisphenol A production process and the phenolic by-product produced in the phenol production process can include one or more selected from the group consisting of bisphenol A, phenol, alpha-methyl styrene, acetophenone, cumyl phenol, and alpha-methyl styrene dimer. As a specific example, the phenolic by-product can include two or more selected from the group consisting of bisphenol A, phenol, alpha-methyl styrene, acetophenone, cumyl phenol, and alpha-methyl styrene dimer, or all of them.

In the phenolic by-product, a ratio of a flow rate of the phenolic by-product produced in the bisphenol A production process to a flow rate of the phenolic by-product produced in the phenol production process can be 1:2 to 10. For example, in the phenolic by-product, the ratio of the flow rate of the phenolic by-product produced in the bisphenol A production process to the flow rate of the phenolic by-product produced in the phenol production process can be 1:2 to 10, 1:4 to 10, or 1:6 to 10. As such, a phenolic by-product in which a content of the phenolic by-product produced in the phenol production process is higher than that of the phenolic by-product produced in the bisphenol A production process is decomposed, which may be preferable in terms of suppressing a load on the decomposition apparatus and reducing energy consumption in the process.

According to an exemplary embodiment of the present invention, the phenol production process and the bisphenol A production process can be performed by including the acid decomposition reaction of the cumene hydroperoxide described above. In this case, since the acid decomposition reaction of the cumene hydroperoxide is performed by including acid, an acid decomposition reaction solution contains acid. Therefore, in order to obtain phenol and acetone from the acid decomposition reaction solution through a process such as distillation, it is required to perform a process of neutralizing the acid decomposition reaction solution.

Prior to separation of the acid decomposition reaction solution, the acid decomposition reaction solution is neutralized by a basic aqueous solution or the like. In this case, in the neutralized acid decomposition reaction solution, a salt is generated by a neutralization reaction between the acid used in the acid decomposition reaction and the base in the basic aqueous solution or the like. A phase of the acid decomposition reaction solution neutralized by the neutralization process is separated into an oil phase and a liquid phase. A separation process for obtaining phenol and acetone from the separated oil phase is performed. In this case, the salt is mostly removed together with the liquid phase, but a part of the salt remains in the oil phase.

Such a salt remains in the phenolic by-product described in the present invention. The salt remaining in the phenolic by-product causes corrosion, occlusion, and deposition in the decomposition apparatus when the phenolic by-product is decomposed to obtain the active ingredient from the phenolic by-product later, which causes a breakdown in the decomposition apparatus. Therefore, prior to the feeding and thermally cracking of the phenolic by-product stream to and in the decomposition apparatus, a step of removing a salt in the phenolic by-product can be further included.

As a method for removing the salt in the phenolic by-product, prior to the decomposition of the phenolic by-product, the salt remaining in the phenolic by-product can be minimized by feeding the phenolic by-product stream to a mixing apparatus and a layer separation apparatus.

The phenolic by-product stream can include one or more selected from the group consisting of bisphenol A, phenol, alpha-methyl styrene, acetophenone, cumyl phenol, and alpha-methyl styrene dimer as described above. As a specific example, the phenolic by-product stream can include two or more selected from the group consisting of bisphenol A, phenol, alpha-methyl styrene, acetophenone, cumyl phenol, and alpha-methyl styrene dimer, or all of them.

According to an exemplary embodiment of the present invention, process water can be mixed with the phenolic by-product in the mixing apparatus. For example, the process water can refer to various aqueous solutions such as an aqueous acidic solution and an aqueous basic solution as well as distilled water.

A pH of the process water can be 3.5 to 7, 3.5 to 5.5, or 3.5 to 4.5. Within this range, solubility of the salt can be improved while preventing corrosion of the mixing apparatus and the layer separation apparatus, and when the phase separation into the oil phase and the liquid phase is performed in the layer separation apparatus, phase separation ability can be improved.

The mixing apparatus can be a mixer for mixing the phenolic by-product and the process water with each other. As a specific example, the mixer can be provided with a line mixer or a static mixer to easily perform the mixing of the phenolic by-product and the process water.

According to an exemplary embodiment of the present invention, the phenolic by-product passed through the mixing apparatus can be fed to the layer separation apparatus, and the phase can be separated into the oil phase and the liquid phase in the layer separation apparatus. Specifically, the layer separation apparatus can be used for separating the process water including the phenolic by-product and the salt to inject only the phenolic by-product from which the salt is removed to the decomposition apparatus 100.

An oil phase stream discharged from the layer separation apparatus is a stream obtained by removing the salt from the phenolic by-product stream, and can be the phenolic by-product stream fed to the decomposition apparatus 100 in the present invention. Accordingly, since a content of the salt in the phenolic by-product stream is minimized, corrosion, occlusion, and deposition in the decomposition apparatus 100 can be prevented when decomposing the phenolic by-product.

According to an exemplary embodiment of the present invention, the phenolic by-product stream can be fed to and thermally cracked in the decomposition apparatus 100. The decomposition performed in the decomposition apparatus 100 can be thermal cracking, and the decomposition apparatus 100 for performing this can be a thermal cracker. As a specific example, the thermal cracker can be a reactor-distillation tower integrated type separation apparatus.

According to an exemplary embodiment of the present invention, in order to separate the active ingredient through a top of the decomposition apparatus 100 and efficiently separate the high-boiling substance including tar through a bottom of the decomposition apparatus 100, the decomposition apparatus 100 can be operated at a pressure of 0.1 KG to 3 KG, 0.5 KG to 2 KG, or 0.5 KG to 1.5 KG. When the decomposition apparatus 100 is operated at the pressure within the above range, acetophenone which is an impurity having a small difference in boiling point from the active ingredient can be discharged through the side discharge stream of the decomposition apparatus 100 as much as possible, such that the active ingredient can be separated through the top of the decomposition apparatus 100 and the high-boiling substance including tar can be efficiently separated through the bottom of the decomposition apparatus 100. In addition, when the decomposition apparatus 100 is operated at the pressure within the above range, an operation temperature of the decomposition apparatus 100 can be kept at a low temperature, such that polymerization of the active ingredient included in the top discharge stream of the decomposition apparatus 100 can be prevented and thermal energy required during the operation of the decomposition apparatus 100 can be reduced.

According to an exemplary embodiment of the present invention, the active ingredient can be separated from the top discharge stream in the decomposition apparatus 100. Specifically, the phenolic by-product can be thermally cracked in the decomposition apparatus 100, and the active ingredient which is a relatively low-boiling substance can be separated from the top discharge stream. In this case, the top discharge stream of the decomposition apparatus 100 can be fed and condensed to and in a condenser (not illustrated), a part of the stream can be circulated to the decomposition apparatus 100, and then a residual stream can be discharged as the active ingredient. For example, the active ingredient can include one or more selected from the group consisting of phenol, alpha-methyl styrene, and cumene.

A vapor pressure of the top discharge stream of the decomposition apparatus 100 in a temperature range of 250° C. to 350° C. can be 5 KG to 30 KG, 9 KG to 20 KG, or 13 KG to KG. Specifically, the top discharge stream of the decomposition apparatus 100 includes one or more selected from the group consisting of phenol, alpha-methyl styrene, and cumene that are relatively low-boiling substances in the phenolic by-product, such that the vapor pressure in the temperature range of 250° C. to 350° C. is relatively high.

According to an exemplary embodiment of the present invention, the bottom discharge stream of the decomposition apparatus 100 can include a high-boiling substance including tar that is generated in the decomposition process of the phenolic by-product due to thermal cracking at a high temperature during the thermal cracking of the phenolic by-product. The high-boiling substance can be recovered to reuse as a fuel or the like.

A part of the bottom discharge stream of the decomposition apparatus 100 is passed through the reboiler 200 and then circulated to the decomposition apparatus 100, and a residual stream of the bottom discharge stream of the decomposition apparatus 100 can be discharged. Specifically, the part of the bottom discharge stream of the decomposition apparatus 100 can be fed and heated to and in the reboiler 200. The heated stream can be discharged from the reboiler 200 and circulated to the decomposition apparatus 100. By doing so, the active ingredient in the bottom discharge stream of the decomposition apparatus 100 can be reduced as much as possible other than tar which is an impurity.

In such a process, a part of the tar included in the bottom discharge stream of the decomposition apparatus 100 fed to the reboiler 200 is accumulated in the reboiler 200, which can cause fouling in the reboiler 200. In the related art, in a case where the tar is accumulated in the reboiler 200 in a certain amount or more, it is difficult to operate the decomposition apparatus 100, and thus, an operation of each of the decomposition apparatus 100 and the reboiler 200 is shut down, the decomposition apparatus 100 and the reboiler 200 are disassembled, and the inside of the reboiler 200 is cleaned. Accordingly, it takes a long time to clean the reboiler 200 due to the time it takes to disassemble the decomposition apparatus 100 and the reboiler 200. Therefore, a shut down time of the decomposition apparatus 100 is increased, which leads to an economical loss and an increase in cost of the active ingredient.

In this regard, in the method of decomposing a phenolic by-product according to the present invention, in order to prevent fouling in the reboiler 200 and extend a fouling cycle of the reboiler 200, the bottom discharge stream of the decomposition apparatus 100 is mixed with the side discharge stream of the decomposition apparatus 100 before the bottom discharge stream of the decomposition apparatus 100 is fed to the reboiler 200, such that the decomposition apparatus 100 and the reboiler 200 may not be required to be disassembled as in the cleaning method of the reboiler 200 in the related art, and a contaminant may not be accumulated in the reboiler 200 due to an action of organic matters in the side discharge stream of the decomposition apparatus 100 as a solvent dissolving tar. In addition, the bottom discharge stream of the decomposition apparatus 100 has a high viscosity due to a large amount of tar contained therein, and thus has poor flowability. However, as in the present invention, the bottom discharge stream of the decomposition apparatus 100 and the side discharge stream of the decomposition apparatus 100 are mixed with each other and discharged, which can improve the flowability.

The side discharge stream of the decomposition apparatus 100 is a stream discharged from a side of the decomposition apparatus 100, and can include one or more selected from the group consisting of phenol, acetophenone, alpha-methyl styrene, and cumene. As a specific example, the side discharge stream of the decomposition apparatus 100 can include phenol, acetophenone, alpha-methyl styrene, and cumene.

The decomposition apparatus 100 can be a multi-stage decomposition apparatus. In this case, the side discharge stream of the decomposition apparatus 100 can be discharged through a stage corresponding to 25% to 90%, 40% to 90%, or 50% to 90% of the total stages of the decomposition apparatus 100. In this case, the amount of the acetophenone discharged through the top discharge stream of the decomposition apparatus 100 can be significantly reduced.

The acetophenone can be included in the side discharge stream of the decomposition apparatus 100 in an amount of wt % or more. For example, the acetophenone can be included in the side discharge stream of the decomposition apparatus 100 in an amount of 40 wt % to 99 wt %, 55 wt % to 99 wt %, or 60 wt % to 99 wt %. The acetophenone is an organic matter included in the phenolic by-product stream, and acts as an impurity in contrast to the active ingredient obtained by the phenolic by-product decomposition reaction. Accordingly, it is preferable that a content of the acetophenone in the active ingredient is minimized. Therefore, in a case where the acetophenone is included in the side discharge stream of the decomposition apparatus 100 in an amount of 40 wt % or more according to the present invention, when the side discharge stream of the decomposition apparatus 100 is fed to a reboiler 200 described below, the contaminant accumulated in the reboiler 200 due to the high-boiling substance can be effectively removed in a short time, and the content of the acetophenone in the active ingredient obtained by the phenolic by-product decomposition reaction can be minimized, which is advantageous in obtaining the active ingredient.

Since the organic matter included in the side discharge stream of the decomposition apparatus 100 has a composition, a temperature, and the like suitable for dissolving the contaminant accumulated in the reboiler 200, the contaminant accumulated on an inner wall and a pipe of the reboiler 200 can be effectively dissolved.

A vapor pressure of the side discharge stream of the decomposition apparatus 100 in a temperature range of 250° C. to 350° C. can be 2 KG to 16 KG, 4 KG to 12 KG, or 6 KG to 8 KG. Specifically, the side discharge stream of the decomposition apparatus 100 includes a substance having a relatively high boiling point as compared to the top discharge stream of the decomposition apparatus 100 due to a high content of the acetophenone therein, such that the vapor pressure in the temperature range of 250° C. to 350° C. is relatively low.

According to an exemplary embodiment of the present invention, the bottom discharge stream of the decomposition apparatus 100 and the side discharge stream of the decomposition apparatus 100 can form a mixed stream, a part of the mixed stream can pass through the reboiler 200 and circulated to the decomposition apparatus 100, and a residual stream can be discharged. In this case, the mixed stream can be a mixture in which a ratio of a flow rate of the side discharge stream of the decomposition apparatus 100 to a flow rate of the bottom discharge stream of the decomposition apparatus 100 is 0.05 to 1.0. For example, the ratio of the flow rate of the side discharge stream of the decomposition apparatus 100 fed to the reboiler 200 to the flow rate of the bottom discharge stream of the decomposition apparatus 100 can be 0.08 to 0.95, 0.1 to 0.75, 0.5 to 0.8, or 0.4 to 0.65. The mixed stream is formed by mixing the bottom discharge stream of the decomposition apparatus 100 and the side discharge stream of the decomposition apparatus 100 with each other at the flow rate within the above range, and the mixed stream is fed to the reboiler 200, such that the contaminant that fouls the reboiler 200 is dissolved. Therefore, the fouling cycle of the reboiler 200 can be extended.

The reason why the side discharge stream of the decomposition apparatus 100 is mixed with the bottom discharge stream of the decomposition apparatus 100 is that the contaminant accumulated on the inner wall, the pipe, and the like of the reboiler 200 are effectively dissolved and removed because the organic matter included in the side discharge stream of the decomposition apparatus 100 has the composition, the temperature, and the like suitable for dissolving the contaminant accumulated in the reboiler 200.

According to an exemplary embodiment of the present invention, as described above, the decomposition apparatus 100 is operated at 0.1 KG to 3 KG. Thus, a stream discharged from the decomposition apparatus 100, for example, a pressure of each of the top discharge stream, the side discharge stream, and the bottom discharge stream of the decomposition apparatus 100 can also be 0.1 KG to 3 KG. However, when each of the streams passes through the reboiler 200 to be heated at a temperature of about 250° C. to 350° C. in the above pressure range, components in each of the streams are evaporated. Thus, heat exchange efficiency in the reboiler 200 may be significantly reduced, and pressure drop may occur due to gas-liquid mixed flow.

In this regard, in the present invention, the side discharge stream of the decomposition apparatus 100 and the bottom discharge stream of the decomposition apparatus 100 are pressurized so that the streams are prevented from being evaporated and are stably circulated in the reboiler 200. For example, each of the side discharge stream of the decomposition apparatus 100 and the bottom discharge stream of the decomposition apparatus 100 can be pressurized using a pump 300. Specifically, before the mixed stream is formed by mixing the side discharge stream of the decomposition apparatus 100 and the bottom discharge stream of the decomposition apparatus 100 with each other, each of the streams can be passed through the pump 300 and pressurized to 2 KG to 16 KG, 4 KG to 12 KG, or 6 KG to 8 KG. By doing so, a pressure of the part of the mixed stream fed to the reboiler 200 can be 2 KG to 16 KG, 4 KG to 12 KG, or 6 KG to 8 KG. Therefore, the evaporation of the stream passing through the reboiler 200 heated at a temperature of about 250° C. to 350° C. can be prevented, and the contaminant that fouls the reboiler 200 can be dissolved and removed.

According to an exemplary embodiment of the present invention, in the method of decomposing a phenolic by-product, a distillation column (not illustrated), a condenser (not illustrated), a reboiler (not illustrated), a valve (not illustrated), a pump (not illustrated), a separator (not illustrated), a mixer (not illustrated), and the like can be additionally installed, if necessary.

Hereinabove, the method of decomposing a phenolic by-product according to the present invention has been described and illustrated in the drawing. However, the description and the illustration of the drawing are for only essential components for understating the present invention, and processes and apparatuses not separately described and illustrated may be properly applicable and used for implementing the method of decomposing a phenolic by-product, in addition to the processes and apparatuses described and illustrated in the drawing.

Hereinafter, the present invention will be described in more detail by examples. However, the following examples are provided for illustrating the present invention. It is apparent to a person skilled in the art that various modifications and alterations may be made without departing from the scope and spirit of the present invention, and the scope of the present invention is not limited thereto.

EXAMPLES

Example 1

Figure 1:
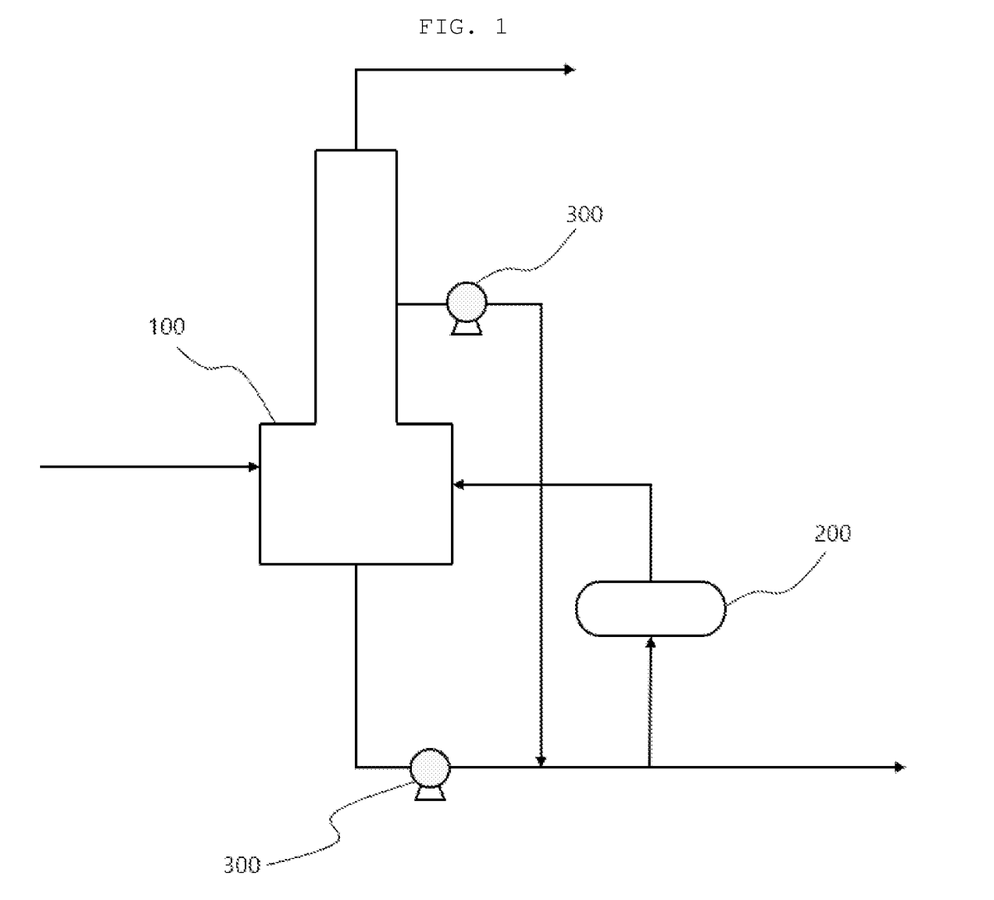
FIG. 1 is a process flow diagram of a method of decomposing a phenolic by-product according to an exemplary embodiment of the present invention.

A phenolic by-product was decomposed according to a process flow diagram illustrated in FIG. 1. Specifically, a phenolic by-product stream of a composition shown in Table 1 produced in a phenol production process was fed to and thermally cracked in a decomposition apparatus 100 operated at 0.1 KG and a flow rate of 1,000 kg/hr, and active ingredients of compositions shown in Table 2 were recovered from a top discharge stream.

Each of a bottom discharge stream of the decomposition apparatus 100 and a side discharge stream of the decomposition apparatus 100 was passed through a pump 300 and pressurized to 6.8 KG, and the bottom discharge stream of the decomposition apparatus 100 and the side discharge stream of the decomposition apparatus 100 that were passed through the pump 300 were mixed with each other to form a mixed stream. In this case, the ratio of a flow rate of the side discharge stream of the decomposition apparatus 100 to a flow rate of the bottom discharge stream of the decomposition apparatus 100 was controlled to 0.5. A composition of the side discharge stream is shown in Table 2.

A part of the mixed stream was passed through a reboiler 200 and circulated to the decomposition apparatus 100, and a residual stream was discharged. In this case, a heating temperature of the reboiler 200 was set to 300° C.

TABLE 1

| Classification | | Phenolic by-product stream |
|---|---|---|
| Phenol | (wt %) | 4.85 |
| Alpha-methyl styrene | (wt %) | 7.14 |
| Cumene | (wt %) | 0.00 |
| Acetophenone | (wt %) | 11.60 |
| Cumyl phenol | (wt %) | 15.32 |
| Alpha-methyl styrene dimer | (wt %) | 10.74 |
| Bisphenol A | (wt %) | 11.56 |
| Etc. | (wt %) | 38.79 |
| Total | (wt %) | 100.00 |

TABLE 2

| Classification | | Top discharge stream of decomposition apparatus | Side discharge stream of decomposition apparatus |
|---|---|---|---|
| Phenol | (wt %) | 32.99 | 19.87 |
| Alpha-methyl styrene | (wt %) | 50.07 | 5.92 |
| Cumene | (wt %) | 11.83 | 0.94 |
| Acetophenone | (wt %) | 0.01 | 46.75 |
| Isopropyl phenol | (wt %) | 0.00 | 26.19 |
| Cumyl phenol | (wt %) | 0.00 | 0.00 |
| Alpha-methyl styrene dimer | (wt %) | 0.00 | 0.00 |
| Bisphenol A | (wt %) | 0.00 | 0.00 |
| Etc. | (wt %) | 5.10 | 0.33 |
| Total | (wt %) | 100.00 | 100.00 |

Example 2

Example 2 was performed in the same manner as that of Example 1, except that the ratio of the flow rate of the side discharge stream of the decomposition apparatus 100 to the flow rate of the bottom discharge stream of the decomposition apparatus 100, when forming the mixed stream, was controlled to 0.8.

Example 3

Example 3 was performed in the same manner as that of Example 1, except that the ratio of the flow rate of the side discharge stream of the decomposition apparatus 100 to the flow rate of the bottom discharge stream of the decomposition apparatus 100, when forming the mixed stream, was controlled to 1.0.

Example 4

Example 4 was performed in the same manner as that of Example 1, except that the ratio of the flow rate of the side discharge stream of the decomposition apparatus 100 to the flow rate of the bottom discharge stream of the decomposition apparatus 100, when forming the mixed stream, was controlled to 0.2.

COMPARATIVE EXAMPLES

Comparative Example 1

Figure 2:
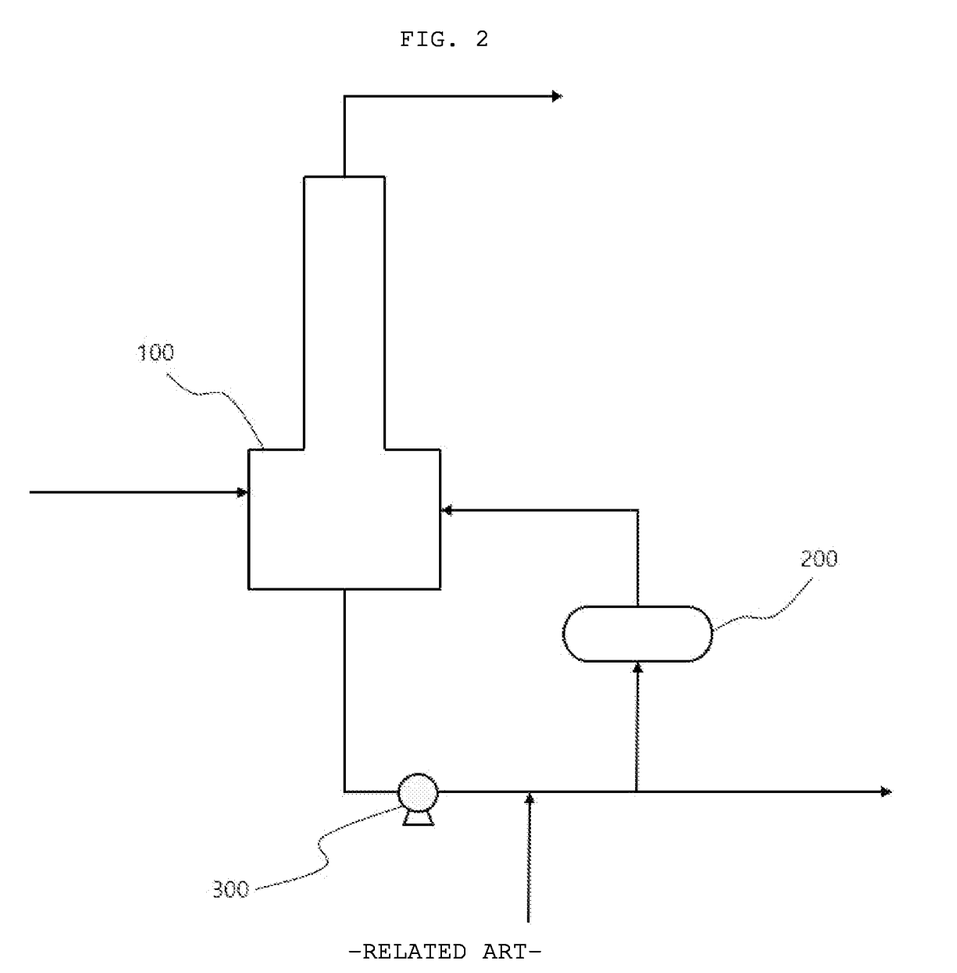
FIGS. 2 and 3 are process flow diagrams of a method of decomposing a phenolic by-product according to Comparative Examples.

A phenolic by-product was decomposed according to a process flow diagram illustrated in FIG. 2. Specifically, a phenolic by-product stream of a composition shown in Table 1 was fed to and thermally cracked in a decomposition apparatus 100 operated at a flow rate of 1,000 kg/hr and an atmospheric pressure, and active ingredients of compositions shown in Table 2 were recovered from a top discharge stream.

A bottom discharge stream of the decomposition apparatus 100 was passed through a pump 300 and pressurized to 9.5 KG, and then was mixed with a stream of a composition shown in Table 3 to form a mixed stream, the stream being an organic layer of an acetone product column (APC) BTM separator fed at a pressure of 9.5 KG. In this case, the ratio of a flow rate of a stream of the organic layer of the APC BTM separator to a flow rate of the bottom discharge stream of the decomposition apparatus 100 was controlled to 0.5.

A part of the mixed stream was passed through a reboiler 200 and circulated to the decomposition apparatus 100, and a residual stream was discharged. In this case, a heating temperature of the reboiler 200 was set to 300° C.

TABLE 3

| Classification | | Organic layer of APC BTM separator |
|---|---|---|
| Alpha-methyl styrene | (wt %) | 20.00 |
| Cumene | (wt %) | 80.00 |
| Total | (wt %) | 100.00 |

Comparative Example 2

Figure 3:
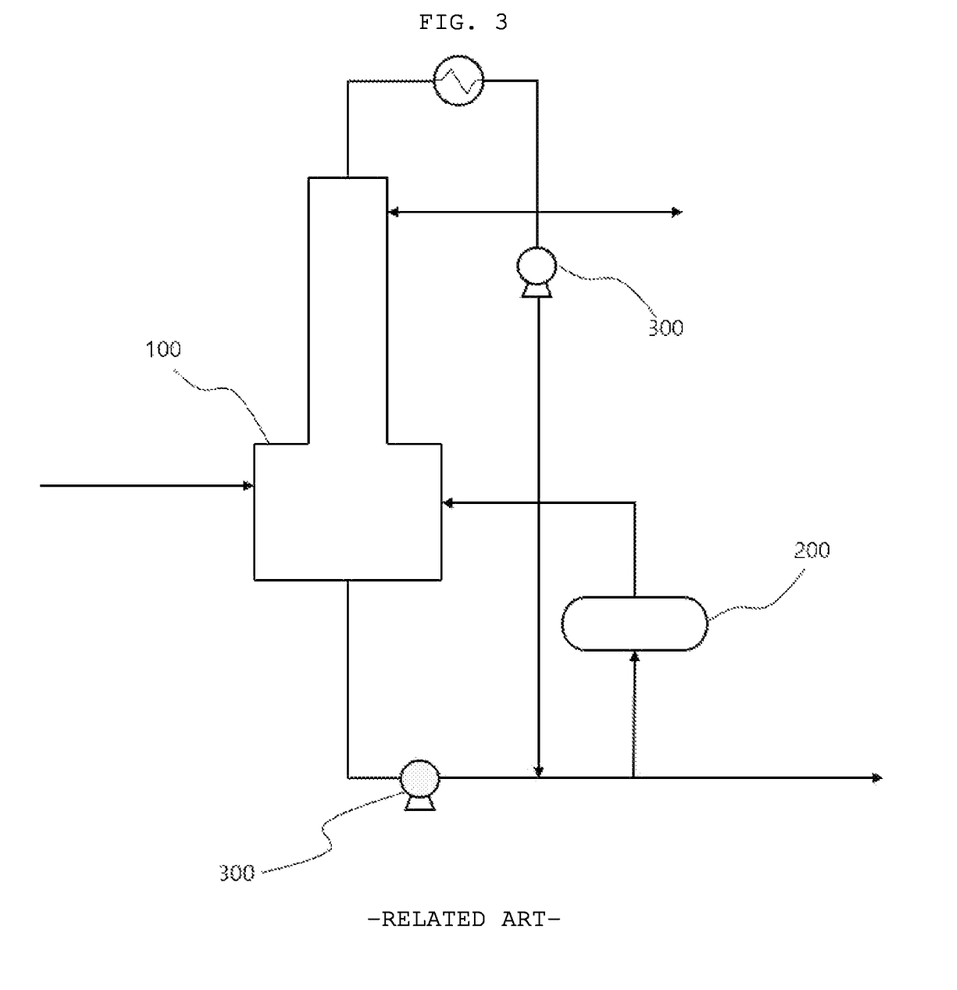

A phenolic by-product was decomposed according to a process flow diagram illustrated in FIG. 3. Specifically, a phenolic by-product stream of a composition shown in Table 1 was fed to and thermally cracked in a decomposition apparatus 100 operated at a flow rate of 1,000 kg/hr and an atmospheric pressure, and active ingredients of compositions shown in Table 2 were recovered from a top discharge stream.

Each of a bottom discharge stream of the decomposition apparatus 100 and a top discharge stream of the decomposition apparatus 100 was passed through a pump 300 and pressurized to 14.5 KG, and the bottom discharge stream of the decomposition apparatus 100 and the top discharge stream of the decomposition apparatus 100 that were passed through the pump 300 were mixed with each other to form a mixed stream. In this case, the ratio of a flow rate of the top discharge stream of the decomposition apparatus 100 to a flow rate of the bottom discharge stream of the decomposition apparatus 100 was controlled to 0.5.

A part of the mixed stream was passed through a reboiler 200 and circulated to the decomposition apparatus 100, and a residual stream was discharged. In this case, a heating temperature of the reboiler 200 was set to 300° C.

Comparative Example 3

Comparative Example 3 was performed in the same manner as that of Example 1, except that the mixed stream was formed by mixing the bottom discharge stream of the decomposition apparatus 100 and the side discharge stream of the decomposition apparatus 100 with each other at an atmospheric pressure without passing through the pump 300 in Example 1.

In this case, the operation was not stable due to evaporation of the mixed stream while passing through the reboiler 200, the flow rate of the stream to be circulated to the reboiler 200 was reduced and a transfer problem occurred due to non-use of the pump, and the fouling cycle was shortened as a retention time was increased.

EXPERIMENTAL EXAMPLE

Experimental Example 1

In Examples 1 to 4 and Comparative Examples 1 and 2, a vapor pressure (KG) of the stream mixed with the bottom discharge stream at 300° C. and energy consumption (Mcal) of the stream circulated in the reboiler 200 were calculated by using literature data. The fouling cycle due to a contaminant (tar) that fouls the reboiler 200 was measured by the following method. The results are shown in Table 4.

Fouling cycle: the operation of the reboiler 200 was suspended, and a point in time when heat exchange efficiency was decreased by 50% or less was measured as a cycle in which the reboiler 200 is required to be cleaned.

TABLE 4

|  | Example 1 | Example 2 | Example 3 | Example 4 | Comparative Example 1 | Comparative Example 2 |
|---|---|---|---|---|---|---|
| Vapor pressure | 6.8 | 6.8 | 6.8 | 6.8 | 9.5 | 14.5 |
| Energy consumption | 3.0 | 4.8 | 6.0 | 1.2 | 10 | 14 |
| Fouling cycle | Three weeks | Three weeks | Three weeks | Two weeks | One week | One week |

Referring to Table 4, it was confirmed that in the step of thermally cracking the phenolic by-product produced in the phenol production process and the mixture of the phenolic by-product produced in the phenol production process and the phenolic by-product produced in the bisphenol A production process by the method according to the present invention, in a case where the bottom discharge stream of the decomposition apparatus 100 and the side discharge stream of the decomposition apparatus 100 were pressurized and mixed with each other and a part of the mixed stream was circulated to the reboiler 200, the mixed stream was circulated at a relatively low pressure without evaporation. In addition, it was confirmed that in a case where the mixed stream was circulated through the reboiler 200, the energy consumption to be used was relatively small. In addition, it could be confirmed that the solubility to the contaminant that fouls the reboiler 200, i.e., tar, was excellent, and thus, the fouling cycle was extended.

In particular, it could be confirmed that in Examples 1 and 2 in which the ratio of the flow rate of the side discharge stream of the decomposition apparatus 100 to the flow rate of the bottom discharge stream of the decomposition apparatus 100 was controlled to 0.5 to 0.8, the energy consumption was relatively small and the fouling cycle was extended. In addition, in Example 3 in which the ratio of the flow rate of the side discharge stream of the decomposition apparatus 100 to the flow rate of the bottom discharge stream of the decomposition apparatus 100 was controlled to 1.0, the fouling cycle was extended, but the energy consumption was slightly increased. In addition, in Example 4 in which the ratio of the flow rate of the side discharge stream of the decomposition apparatus 100 to the flow rate of the bottom discharge stream of the decomposition apparatus 100 was controlled to 0.2, the energy consumption was reduced, but the fouling cycle was slightly shortened.

In contrast, in Comparative Example 1 in which the bottom discharge stream of the decomposition apparatus 100 and the organic layer of the APC BTM separator were mixed with each other and the mixed stream was fed to the reboiler 200 and circulated to the decomposition apparatus 100, the fouling cycle was short due to a low solubility to the contaminant, and thus, the stream was required to be pressurized to a high pressure of 9.5 KG or more to circulate the mixed stream using the reboiler 200 without evaporation.

In addition, in Comparative Example 2 in which the bottom discharge stream of the decomposition apparatus 100 and the top discharge stream of the decomposition apparatus 100 were mixed with each other and the mixed stream was circulated to the reboiler 200, the fouling cycle was short due to a low solubility to the contaminant, and thus, the stream was required to be pressurized to a very high pressure of 14.5 KG or more to circulate the mixed stream using the reboiler 200 without evaporation.

The invention claimed is:

1. A method of decomposing a phenolic by-product, the method comprising:
   a step of feeding a phenolic by-product stream to a decomposition apparatus, thermally cracking the phenolic by-product in the decomposition apparatus, recovering an active ingredient from a top discharge stream, and discharging a high-boiling substance through a bottom discharge stream;
   a step of pressurizing each of a side discharge stream of the decomposition apparatus and the bottom discharge stream of the decomposition apparatus;
   a step of mixing the pressurized side discharge stream of the decomposition apparatus and the pressurized bottom discharge stream of the decomposition apparatus with each other to form a mixed stream; and
   a step of passing a part of the mixed stream through a reboiler, circulating the part of the mixed stream to the decomposition apparatus, and discharging a residual mixed stream.

2. The method of claim 1, wherein the phenolic by-product includes any one or more of a phenolic by-product produced in a phenol production process and a phenolic by-product produced in a bisphenol A production process.

3. The method of claim 1, wherein the phenolic by-product includes one or more compounds selected from the group consisting of bisphenol A, phenol, alpha-methyl styrene, acetophenone, cumyl phenol, and alpha-methyl styrene dimer.

4. The method of claim 1, wherein the side discharge stream of the decomposition apparatus includes one or more compounds selected from the group consisting of phenol, acetophenone, alpha-methyl styrene, and cumene.

5. The method of claim 1, wherein the side discharge stream of the decomposition apparatus comprises acetophenone in an amount of 40 wt % or more.

6. The method of claim 1, wherein an operation pressure of the decomposition apparatus is 0.1 KG to 3 KG.

7. The method of claim 1, wherein each of the side discharge stream of the decomposition apparatus and the bottom discharge stream of the decomposition apparatus is pressurized to a pressure of 2 KG to 16 KG.

8. The method of claim 1, wherein each of the side discharge stream of the decomposition apparatus and the bottom discharge stream of the decomposition apparatus is pressurized using a pump.

9. The method of claim 1, wherein a pressure of the part of the mixed stream passing through the reboiler is 2 KG to 16 KG.

10. The method of claim 1, wherein a vapor pressure of the side discharge stream of the decomposition apparatus in a temperature range of 250° C. to 350° C. is 2 KG to 16 KG.

11. The method of claim 1, wherein a ratio of a flow rate of the side discharge stream of the decomposition apparatus to a flow rate of the bottom discharge stream of the decomposition apparatus is 0.05 to 1.0.

12. The method of claim 1, wherein the active ingredient includes one or more compounds selected from the group consisting of phenol, alpha-methyl styrene, and cumene.

* * * * *